United States Patent [19]

Monia et al.

[11] Patent Number: 5,563,255
[45] Date of Patent: Oct. 8, 1996

[54] ANTISENSE OLIGONUCLEOTIDE MODULATION OF RAF GENE EXPRESSION

[75] Inventors: Brett P. Monia, Carlsbad; Russell T. Boggs, Cardiff-by-the-Sea, both of Calif.

[73] Assignee: Isis Pharmaceuticals, Inc., Carlsbad, Calif.

[21] Appl. No.: 250,856

[22] Filed: May 31, 1994

[51] Int. Cl.$^6$ ............................ C07H 21/00; C12Q 1/68; A61K 31/70
[52] U.S. Cl. ..................... 536/24.31; 435/6; 536/24.1; 536/24.5
[58] Field of Search ......................... 435/6, 7.21, 7.23; 536/23.1, 23.2, 23.5, 24.3, 24.31, 24.5; 514/44

[56] References Cited

U.S. PATENT DOCUMENTS

| | | | |
|---|---|---|---|
| 4,806,463 | 2/1989 | Goodchild et al. | 435/5 |
| 4,871,838 | 10/1989 | Bos et al. | 536/27 |
| 5,004,810 | 4/1991 | Draper et al. | 536/27 |
| 5,034,506 | 7/1991 | Summerton et al. | 528/391 |
| 5,087,617 | 2/1992 | Smith | 514/44 |
| 5,098,890 | 3/1992 | Gewirtz et al. | 514/44 |
| 5,135,917 | 8/1992 | Burch | 514/44 |
| 5,166,195 | 11/1992 | Ecker et al. | 514/44 |
| 5,194,428 | 3/1993 | Agrawal et al. | 514/44 |
| 5,264,423 | 11/1993 | Cohen et al. | 514/44 |
| 5,276,019 | 1/1994 | Cohen et al. | 514/44 |
| 5,286,717 | 2/1994 | Cohen et al. | 514/44 |

FOREIGN PATENT DOCUMENTS

| | | |
|---|---|---|
| WO93/04170 | 3/1993 | WIPO. |
| WO93/06248 | 4/1993 | WIPO. |

OTHER PUBLICATIONS

Sprout "Synthesis of 2'-O-Alkyloligoribonucleotides" in Methods in Molecular Biology, vol. 20, Humana Press 1993, pp. 115–116.

Kasid et al "Effect of Antisense c–raf–1 . . ." Science 243 (1989), 1354–1356.

Kingston "Guanidinium Methods for total RNA preparation" in Current Protocols in Molecular Biology (Supplement 14) John Wiely and Sons, NY.

Anfossi et al., "An oligomer complementary to c–myb–encoded mRNA inhibits proliferation of human myeloid leukemia cell lines", *Proc. Natl. Acad. Sci.* 1989, 86, 3379–3383.

App et al., "Epidermal Growth Factor (EGF) Stimulates Association and Kinase Activity of Raf–1 with the EGF Receptor", *Mol. Cell Biol.* 1991, 11, 913–919.

Holt et al., "An Oligomer Complementary to c–myc mRNA Inhibits Proliferatin of HL–60 Promyelocytic Cells and Induces Differentiation", *Mol. Cell Biol.* 1988, 8, 963–973.

P. E. Nielsen et al., "Sequence–Selective Recognition of DNA by Strand Displacement with a Thymine–Substituted Polyamide", *Science* 1991, 254, 1497.

Rapp et al., "The raf oncogenes", *The Oncogene Handbook*, E. P. Reddy, A. M. Skalka and T. Curran, eds., Elsevier Science Publishers, New York, 1988, pp. 213–253.

Riedel et al., "The Mitogenic response of T cells to interleukin-2 requires Raf-1", *Eur. J. Immunol.* 1993, 23, 3146–3150.

Sambrook et al., "Labeling the 5' Terminus of DNA with Bacteriophage T4 Polynucleotide Kinase", *Molecular Cloning. A Laboratory Manual*, Cold Spring Harbor Laboratory Press, 1989, vol. 2, p. 10.59.

Sambrook et al., "Labeling of Synthetic Oligonucleotides by Phosphorylation with Bacteriophage T4 Polynucleotide Kinase", *Molecular Cloning. A Laboratory Manual*, Cold Spring Harbor Laboratory Press, 1989, vol. 2, pp. 11.31–11.32.

Stanton and Cooper, "Activation of Human raf Transforming Genes by Deletion of Normal Amino–Terminal Coding Sequences", *Mol. Cell. Biol.* 1987, 7, 1171–1179.

Tornkvist et al., "Inhibition of Raf–1 Kinase Expression Abolishes Insulin Stimulation of DNA Synthesis in H4IIE Hepatoma Cells", *J. Biol. Chem.* 1994, 269, 13919–13921.

Wickstrom et al., "Human promyelocytic leukemia HL–60 cell proliferation and c–myc protein expression are inhibited by an antisense pentadecadeoxynucleotide targeted against c–myc mRNA", *Proc. Nat. Acad. Sci.* 1988, 85, 1028–1032.

Bonner et al "The Complete Coding Sequence . . ." Nucleic Acids. Research, 1986, vol. 14, pp. 1009–1015.

Beck et al "The Complete Coding Sequence . . ." Nucleic Acids Research 1986, vol. 15, pp. 595–609.

Milligan et al "Current Concepts in Antisense Drug Design" J. Medicinal Chemistry 1993 vol. 36, pp. 1923–1937.

*Primary Examiner*—George C. Elliott
*Assistant Examiner*—Thomas G. Larson
*Attorney, Agent, or Firm*—Law Offices of Jane Massey Licata

[57] ABSTRACT

Oligonucleotides are provided which are targeted to nucleic acids encoding human raf and capable of inhibiting raf expression. In preferred embodiments, the oligonucleotides are targeted to mRNA encoding human c-raf or human A-raf. The oligonucleotides may have chemical modifications at one or more positions and may be chimeric oligonucleotides. Methods of inhibiting the expression of human raf using oligonucleotides of the invention are also provided. The present invention further comprises methods of detecting the presence of a raf gene using oligonucleotides of the invention, including methods for specific detection of activated truncated raf. Methods of inhibiting hyperproliferation of cells and methods of treating conditions arising from abnormal raf expression which employ oligonucleotides of the invention are also provided.

12 Claims, No Drawings

ANTISENSE OLIGONUCLEOTIDE MODULATION OF RAF GENE EXPRESSION

FIELD OF THE INVENTION

This invention relates to compositions and methods for modulating expression of the raf gene, a naturally present cellular gene which occasionally converts to an activated form that has been implicated in abnormal cell proliferation and tumor formation. This invention is further directed to compositions and methods for the detection of both normal and activated forms of the raf gene, as well as the detection and diagnosis of abnormal expression of the raf gene in cells and tissues. This invention is also directed to methods for inhibiting hyperproliferation of cells; these methods can be used diagnostically or therapeutically. Furthermore, this invention is directed to treatment of conditions arising from activation or other abnormal expression of the raf gene.

BACKGROUND OF THE INVENTION

Alterations in the cellular genes which directly or indirectly control cell growth and differentiation are considered to be the main cause of cancer. There are some thirty families of genes, called oncogenes, which are implicated in human tumor formation. Members of one such family, the raf gene family, are frequently found to be mutated in human tumors. The raf family includes three highly conserved genes termed A-, B- and c-raf (also called raf-1). c-Raf, the best characterized member of the raf family, is the cellular homologue of v-raf, the transforming gene of the murine sarcoma virus 3611. Raf genes encode protein kinases that are thought to play important regulatory roles in signal transduction processes that regulate cell proliferation. Mutation of raf genes causing a truncation or other modification that leads to the expression of raf kinase without a functional negative regulatory domain at the amino-terminal end results in conversion to a form which is implicated in transformation of mammalian cells in culture, and tumor formation. A raf gene having an absent or inactive regulatory domain is said to be "activated." Activated (truncated) raf has been detected in a variety of human cancers including small-cell lung carcinoma, primary stomach cancer, renal cancer, breast cancer, laryngeal cancer, skin fibroblasts from members of a cancer-prone family (Li-Fraumeni syndrome), and in a human glioblastoma cell line. The position of truncation in a number of human carcinomas occurs in the vicinity of exons 7 and 8 and the intervening intron 7 of the c-raf coding region. Rapp et al., *The Oncogene Handbook*, E. P. Reddy, A. M Skalka and T. Curran, eds., Elsevier Science Publishers, New York, 1988, pp. 213–253. Stanton, V. P. and G. M. Cooper, *Mol. Cell. Biol.* 1987, 7, 1171–1179. DNA from these sources contained a transforming activity, identified in most cases as c-raf-1 derived, as determined by DNA transfection of NIH/3T3 cells. In the case of the primary stomach cancer, DNA from normal tissue was not transforming to 3T3 cells. Injection of truncated c-raf protein into serum-starved NIH 3T3 cells induces DNA synthesis and morphological transformation in those cells. App et al., *Mol. Cell Biol.* 1991, 11, 913–919. Abnormal expression of the normal (non-activated) c-raf protein is also believed to play a role in abnormal cell proliferation since it has been reported that 60% of all lung carcinoma cell lines express unusually high levels of normal c-raf mRNA and protein. Rapp et al., *The Oncogene Handbook*, E. P. Reddy, A. M Skalka and T. Curran, eds., Elsevier Science Publishers, New York, 1988, pp. 213–253.

Oligonucleotides have been employed as therapeutic moieties in the treatment of disease states in animals and man. For example, workers in the field have now identified antisense, triplex and other oligonucleotide compositions which are capable of modulating expression of genes implicated in viral, fungal and metabolic diseases.

As examples, U.S. Pat. No. 5,098,890, issued Mar. 24, 1992 in the name of Gewirtz, et al., is directed to antisense oligonucleotides complementary to the c-myb oncogene and antisense oligonucleotide therapies for certain cancerous conditions. U.S. Pat. No. 5,135,917, issued Aug. 4, 1992, provides antisense oligonucleotides that inhibit human interleukin-1 receptor expression. U.S. Pat. No. 5,087,617, issued Feb. 11, 1992, provides methods for treating cancer patients with antisense oligonucleotides. U.S. Pat. No. 5,166,195 issued Nov. 24, 1992 provides oligonucleotide inhibitors of HIV. U.S. Pat. No. 5,004,810, issued Apr. 2, 1991, provides oligomers capable of hybridizing to herpes simplex virus Vmw65 mRNA and inhibiting replication. U.S. Pat. No. 5,194,428, issued Mar. 16, 1993, provides antisense oligonucleotides having antiviral activity against influenzavirus. U.S. Pat. No. 4,806,463, issued Feb. 21, 1989, provides antisense oligonucleotides and methods using them to inhibit HTLV-III replication. U.S. Pat. No. 5,286,717 (Cohen et al.), issued Feb. 15, 1994, is directed to a mixed linkage oligonucleotide phosphorothioates complementary to an oncogene; U.S. Pat. No. 5,276,019 and U.S. Pat. No. 5,264,423 (Cohen et al.) are directed to phosphorothioate oligonucleotide analogs used to prevent replication of foreign nucleic acids in cells. Antisense oligonucleotides have been safely administered to humans and clinical trials of several antisense oligonucleotide drugs are presently underway. It is thus established that oligonucleotides can be useful therapeutic instrumentalities and can be configured to be useful in treatment regimes for treatment of cells and animal subjects, especially humans.

Antisense oligonucleotide inhibition of oncogenes has proven to be a useful tool in understanding the roles of various oncogene families. For example, Holt et al., *Mol. Cell Biol.* 1988, 8, 963–973, have shown that antisense oligonucleotides hybridizing specifically with mRNA transcripts of the oncogene c-myc, when added to cultured HL60 leukemic cells, inhibit proliferation and induce differentiation. Anfossi et al., *Proc. Natl. Acad. Sci.* 1989, 86, 3379–3383, have shown that antisense oligonucleotides specifically hybridizing with mRNA transcripts of the c-myb oncogene inhibit proliferation of human myeloid leukemia cell lines. Wickstrom et al., *Proc. Nat. Acad. Sci.* 1988, 85, 1028–1032, have shown that expression of the protein product of the c-myc oncogene as well as proliferation of HL60 cultured leukemic cells are inhibited by antisense oligonucleotides hybridizing specifically with c-myc mRNA. U.S. Pat. No. 4,871,838 (Bos et al.) discloses molecules useful as probes for detecting a mutation in DNA which encodes a ras protein. An antisense oligonucleotide complementary to the first six codons of human c-raf has been used to demonstrate that the mitogenic response of T cells to interleukin-2 (IL-2) requires c-raf. Cells treated with the oligonucleotide showed a near-total loss of c-raf protein and a substantial reduction in proliferative response to IL-2. Riedel et al., *Eur. J. Immunol.* 1993, 23, 3146–3150. Rapp et al. have disclosed expression vectors containing a raf gene in an antisense orientation downstream of a promoter, and methods of inhibiting raf expression by expressing an antisense Raf gene or a mutated Raf gene in a cell. WO application 93/04170. An antisense oligodeoxyribonucleotide complementary to codons 1–6 of murine c-Raf has been used to abolish insulin stimulation of DNA synthesis in the rat hepatoma cell line H4IIE. Tornkvist et al., *J. Biol. Chem.* 1994, 269, 13919–13921. WO Application 93/06248 discloses methods for identifying an individual at increased risk of developing cancer and for determining a prognosis and proper treatment of patients afflicted with cancer comprising amplifying a region of the c-raf gene and analyzing it for evidence of mutation. Thus there remains a long-felt need for improved compositions and methods for inhibiting abnormal raf gene expression.

SUMMARY OF THE INVENTION

The present invention provides oligonucleotides which are targeted to nucleic acids encoding human raf and are capable of inhibiting raf expression. The present invention also provides chimeric oligonucleotides targeted to nucleic acids encoding human raf. The oligonucleotides of the invention are believed to be useful both diagnostically and therapeutically, and are believed to be particularly useful in the methods of the present invention.

The present invention also comprises methods of inhibiting the expression of human raf. These methods are believed to be useful both therapeutically and diagnostically as a consequence of the association between abnormal raf expression and hyperproliferation. These methods are also useful as tools, for example for detecting and determining the role of raf expression in various cell functions and physiological processes and conditions and for diagnosing conditions associated with abnormal raf expression.

The present invention further comprises methods of detecting the presence of a raf gene using the oligonucleotides of the invention. Also provided are methods of detecting activated truncated raf based on differential oligonucleotide binding. These methods are believed to be useful in assays and diagnostics, for example in diagnosing conditions arising from ras activation.

The present invention also comprises methods of inhibiting hyperproliferation of cells using oligonucleotides of the invention. These methods are believed to be useful, for example in diagnosing raf-associated cell hyperproliferation. Methods of treating conditions arising from abnormal raf expression are also provided. These methods employ the oligonucleotides of the invention. These methods are believed to be useful both therapeutically and as clinical research and diagnostic tools.

DETAILED DESCRIPTION OF THE INVENTION

Malignant tumors develop through a series of stepwise, progressive changes that lead to the loss of growth control characteristic of cancer cells, i.e., continuous unregulated proliferation, the ability to invade surrounding tissues, and the ability to metastasize to different organ sites. Carefully controlled in vitro studies have helped define the factors that characterize the growth of normal and neoplastic cells and have led to the identification of specific proteins that control cell growth and differentiation. In addition, the ability to study cell transformation in carefully controlled, quantitative in vitro assays has led to the identification of specific genes capable of inducing the transformed cell phenotype. Such cancer-causing genes, or oncogenes, are believed to acquire transformation-inducing properties through mutations leading to changes in the regulation of expression of their protein products. In some cases such changes occur in non-coding DNA regulatory domains, such as promoters and enhancers, leading to alterations in the transcriptional activity of oncogenes, resulting in over- or under-expression of their gene products. In other cases, gene mutations occur within the coding regions of oncogenes, leading to the production of altered gene products that are inactive, overactive, or exhibit an activity that is different from the normal (wild-type) gene product.

To date, more than 30 cellular oncogene families have been identified. The raf oncogenes are members of a gene family which encode related proteins termed A-, B- and c-raf. Raf genes code for highly conserved serine-threonine-specific protein kinases. These enzymes are differentially expressed; c-raf, the most thoroughly characterized, is expressed in all organs and in all cell lines that have been examined. A- and B-raf are expressed in urogenital and brain tissues, respectively. c-raf protein kinase activity and subcellular distribution are regulated by mitogens via phosphorylation. Various growth factors, including epidermal growth factor, acidic fibroblast growth factor, platelet-derived growth factor, insulin, granulocyte-macrophage colony-stimulating factor, interleukin-2, interleukin, 3 and erythropoietin, have been shown to induce phosphorylation of c-raf. Thus c-raf is believed to play a fundamental role in the normal cellular signal transduction pathway, coupling a multitude of growth factors to their net effect, cellular proliferation.

All three raf proteins contain three highly conserved functional domains. The first (amino-terminal) domain is rich in cysteine residues and functions as a negative regulator of the kinase activity of the protein. The second domain is a serine-threonine rich region that undergoes hyperphosphorylation in response to certain stimuli and the third is the kinase domain. Mutations of the regulatory domain due to inactivation or truncation lead to oncogenic activation of the raf kinase, i.e., conversion to a form which has been implicated in cellular growth transformation. It is believed that such deregulation of normal raf protein function is responsible for the transformation from normal to malignant growth. Abnormally high levels of expression of the normal (non-activated) raf protein may also lead to such transformation.

It is presently believed that elimination or reduction of abnormal raf gene expression may reverse abnormal cell proliferation. There is a great desire to provide compositions of matter which can modulate the abnormal expression of the raf gene. "Abnormal" gene expression is defined here either as expression of the activated raf product or as an unusually high level of expression of the normal raf product. It is greatly desired to provide methods of detection of the raf gene in cells, tissues and animals. It is also desired to provide methods of diagnosis and treatment of conditions arising from abnormal raf gene expression. In addition, kits and reagents for detection and study of the raf gene are desired.

The present invention employs oligonucleotides targeted to nucleic acids encoding raf. This relationship between an oligonucleotide and its complementary nucleic acid target to which it hybridizes is commonly referred to as "antisense." "Targeting" an oligonucleotide to a chosen nucleic acid target, in the context of this invention, is a multistep process. The process usually begins with identifying a nucleic acid sequence whose function is to be modulated. This may be, as examples, a cellular gene (or mRNA made from the gene) whose expression is associated with a particular disease state, or a foreign nucleic acid from an infectious agent. In the present invention, the target is a nucleic acid encoding raf; in other words, the raf gene or mRNA expressed from the raf gene. The targeting process also includes determination of a site or sites within the nucleic acid sequence for the oligonucleotide interaction to occur such that the desired effect—modulation of gene expression—will result. Once the target site or sites have been identified, oligonucleotides are chosen which are sufficiently complementary to the target, i.e., hybridize sufficiently well and with sufficient specificity, to give the desired modulation.

In the context of this invention "modulation" means either inhibition or stimulation. Inhibition of abnormal raf gene expression is presently the preferred form of modulation. This modulation can be measured in ways which are routine in the art, for example by Northern blot assay of mRNA expression or Western blot assay of protein expression as taught in the examples of the instant application. Effects on cell proliferation or tumor cell growth can also be measured, as taught in the examples of the instant application. "Hybridization," in the context of this invention, means hydrogen bonding, also known as Watson-Crick base pairing, between complementary bases, usually on opposite nucleic acid strands or two regions of a nucleic acid strand. Guanine and cytosine are examples of complementary bases which are known to form three hydrogen bonds between them. Adenine and thymine are examples of complementary bases which form two hydrogen bonds between them. "Specifically hybridizable" and "complementary" are terms which are used to indicate a sufficient degree of complementarity such that stable and specific binding occurs between the DNA or RNA target and the oligonucleotide. It is understood that an oligonucleotide need not be 100% complementary to its target nucleic acid sequence to be specifically hybridizable. An oligonucleotide is specifically hybridizable when binding of the oligonucleotide to the target interferes with the normal function of the target molecule to cause a loss of utility, and there is a sufficient degree of complementarity to avoid non-specific binding of the oligonucleotide to non-target sequences under conditions in which specific binding is desired, i.e., under physiological conditions in the case of in vivo assays or therapeutic treatment, or, in the case of in vitro assays, under conditions in which the assays are conducted.

In preferred embodiments of this invention, oligonucleotides are provided which are targeted to mRNA encoding c-raf and A-raf. In accordance with this invention, persons of ordinary skill in the art will understand that mRNA includes not only the coding region which carries the information to encode a protein using the three letter genetic code, but also associated ribonucleotides which form a region known to such persons as the 5'-untranslated region, the 3'-untranslated region, the 5' cap region, intron regions and intron/exon or splice junction ribonucleotides. Thus, oligonucleotides may be formulated in accordance with this invention which are targeted wholly or in part to these associated ribonucleotides as well as to the coding ribonucleotides. In preferred embodiments, the oligonucleotide is targeted to a translation initiation site (AUG codon) or sequences in the 5'- or 3'-untranslated region of the human c-raf mRNA. The functions of messenger RNA to be interfered with include all vital functions such as translocation of the RNA to the site for protein translation, actual translation of protein from the RNA, splicing or maturation of the RNA and possibly even independent catalytic activity which may be engaged in by the RNA. The overall effect of such interference with the RNA function is to cause interference with raf protein expression.

The present invention provides oligonucleotides for modulation of raf gene expression. Such oligonucleotides are targeted to nucleic acids encoding raf. Oligonucleotides and methods for modulation of c-raf and A-raf are presently preferred; however, compositions and methods for modulating expression of other forms of raf are also believed to have utility and are comprehended by this invention. As hereinbefore defined, "modulation" means either inhibition or stimulation. Inhibition of abnormal raf gene expression is presently the preferred form of modulation.

In the context of this invention, the term "oligonucleotide" refers to an oligomer or polymer of nucleotide or nucleoside monomers consisting of naturally occurring bases, sugars and intersugar (backbone) linkages. The term "oligonucleotide" also includes oligomers comprising non-naturally occurring monomers, or portions thereof, which function similarly. Such modified or substituted oligonucleotides are often preferred over native forms because of properties such as, for example, enhanced cellular uptake and increased stability in the presence of nucleases.

Certain preferred oligonucleotides of this invention are chimeric oligonucleotides. "Chimeric oligonucleotides" or "chimeras", in the context of this invention, are oligonucleotides which contain two or more chemically distinct regions, each made up of at least one nucleotide. These oligonucleotides typically contain at least one region of modified nucleotides that confers one or more beneficial properties (such as, for example, increased nuclease resistance, increased uptake into cells, increased binding affinity for the RNA target) and a region that is a substrate for RNase H cleavage. In one preferred embodiment, a chimeric oligonucleotide comprises at least one region modified to increase target binding affinity, and, usually, a region that acts as a substrate for RNAse H. Affinity of an oligonucleotide for its target (in this case a nucleic acid encoding raf) is routinely determined by measuring the Tm of an oligonucleotide/target pair, which is the temperature at which the oligonucleotide and target dissociate; dissociation is detected spectrophotometrically. The higher the Tm, the greater the affinity of the oligonucleotide for the target. In a more preferred embodiment, the region of the oligonucleotide which is modified to increase raf mRNA binding affinity comprises at least one nucleotide modified at the 2' position of the sugar, most preferably a 2'-O-alkyl or 2'-fluoro-modified nucleotide. Such modifications are routinely incorporated into oligonucleotides and these oligonucleotides have been shown to have a higher Tm (i.e., higher target binding affinity) than 2'-deoxyoligonucleotides against a given target. The effect of such increased affinity is to greatly enhance antisense oligonucleotide inhibition of raf gene expression. RNAse H is a cellular endonuclease that cleaves the RNA strand of RNA:DNA duplexes; activation of this enzyme therefore results in cleavage of the RNA target, and thus can greatly enhance the efficiency of antisense inhibition. Cleavage of the RNA target can be routinely demonstrated by gel electrophoresis. In another preferred embodiment, the chimeric oligonucleotide is also modified to enhance nuclease resistance. Cells contain a variety of exo- and endo-nucleases which can degrade nucleic acids. A number of nucleotide and nucleoside modifications have been shown to make the oligonucleotide into which they are incorporated more resistant to nuclease digestion than the native oligodeoxynucleotide. Nuclease resistance is routinely measured by incubating oligonucleotides with cellular extracts or isolated nuclease solutions and measuring the extent of intact oligonucleotide remaining over time, usually by gel electrophoresis. Oligonucleotides which have been modified to enhance their nuclease resistance survive intact for a longer time than unmodified oligonucleotides. A variety of oligonucleotide modifications have been demonstrated to enhance or confer nuclease resistance. Oligonucleotides which contain at least one phosphorothioate modification are presently more preferred. In some cases, oligonucleotide modifications which enhance target binding affinity are also, independently, able to enhance nuclease resistance.

Specific examples of some preferred oligonucleotides envisioned for this invention may contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid or peptide-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, *Science* 1991, 254, 1497. Other preferred oligonucleotides may contain alkyl and halogen-substituted sugar moieties comprising one of the following at the 2' position: OH, SH, $SCH_3$, F, OCN, $OCH_3OCH_3$, $OCH_3O(CH_2)_nCH_3$, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a cholesteryl group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group. Other preferred embodiments may include at least one modified base form or "universal base" such as inosine.

The oligonucleotides in accordance with this invention preferably are from about 8 to about 50 nucleotides in length. In the context of this invention it is understood that this encompasses non-naturally occurring oligomers as hereinbefore described, having 8 to 50 monomers.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed; the actual synthesis of the oligonucleotides is well within the talents of the routineer. It is also well known to use similar techniques to prepare other oligonucleotides such as the phosphorothioates and alkylated derivatives. It is also well known to use similar techniques and commercially available modified amidites and controlled-pore glass (CPG) products such as biotin, fluorescein, acridine or psoralen-modified amidites and/or CPG (available from Glen Research, Sterling Va.) to synthesize fluorescently labeled, biotinylated or other modified oligonucleotides such as cholesterol-modified oligonucleotides.

It has now been found that certain oligonucleotides targeted to portions of the c-raf mRNA are particularly useful for inhibiting raf expression and for interfering with cell hyperproliferation. Methods for inhibiting c-raf expression using antisense oligonucleotides are, likewise, useful for interfering with cell hyperproliferation. In the methods of the invention, tissues or cells are contacted with oligonucleotides. In the context of this invention, to "contact" tissues or cells with an oligonucleotide or oligonucleotides means to add the oligonucleotide(s), usually in a liquid carrier, to a cell suspension or tissue sample, either in vitro or ex vivo, or to administer the oligonucleotide(s) to cells or tissues within an animal.

For therapeutics, methods of modulating cell proliferation are provided. The formulation of therapeutic compositions and their subsequent administration is believed to be within the skill in the art. In general, for therapeutics, a patient suspected of needing such therapy is given an oligonucleotide in accordance with the invention, commonly in a pharmaceutically acceptable carrier, in amounts and for periods which will vary depending upon the nature of the particular disease, its severity and the patient's overall condition. The pharmaceutical compositions of this invention may be administered in a number of ways depending upon whether local or systemic treatment is desired, and upon the area to be treated. Administration may be topical (including ophthalmic, vaginal, rectal, intranasal), oral, or parenteral, for example by intravenous drip, subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

In addition to such pharmaceutical carriers, cationic lipids may be included in the formulation to facilitate oligonucleotide uptake. One such composition shown to facilitate uptake is LIPOFECTIN (a 1:1 liposome formulation of the cationic lipid N-[1-( 2,3-dioleyloxy)propyl]-N,N,N-trimethylammonium chloride (DOTMA) and dioleoyl phosphatidylethanolamine (DOPE)) (BRL, Bethesda Md.).

Dosing is dependent on severity and responsiveness of the condition to be treated, with course of treatment lasting from several days to several months or until a cure is effected or a diminution of disease state is achieved. Optimal dosing schedules can be calculated from measurements of drug accumulation in the body. Persons of ordinary skill can easily determine optimum dosages, dosing methodologies and repetition rates. Optimum dosages may vary depending on the relative potency of individual oligonucleotides, and can generally be estimated based on EC50's in in vitro and in vivo animal studies.

The present invention is also suitable for diagnosing abnormal proliferative states in tissue or other samples from patients suspected of having a hyperproliferative disease such as cancer, psoriasis or blood vessel restenosis or atherosclerosis. The ability of the oligonucleotides of the present invention to inhibit cell proliferation may be employed to diagnose such states. A number of assays may be formulated employing the present invention, which assays will commonly comprise contacting a tissue sample with an oligonucleotide of the invention under conditions selected to permit detection and, usually, quantitation of such inhibition. Similarly, the present invention can be used to distinguish raf-associated tumors from tumors having other etiologies, in order that an efficacious treatment regime can be designed.

The oligonucleotides of this invention may also be used for research purposes. Thus, the specific hybridization exhibited by the oligonucleotides may be used for assays, purifications, cellular product preparations and in other methodologies which may be appreciated by persons of ordinary skill in the art.

The oligonucleotides of the invention are also useful for detection and diagnosis of abnormal raf expression. For example, radiolabeled oligonucleotides can be prepared by $^{32}$P labeling at the 5' end with polynucleotide kinase. Sambrook et al., *Molecular Cloning. A Laboratory Manual*, Cold Spring Harbor Laboratory Press, 1989, Volume 2, pg. 10.59. Radiolabeled oligonucleotides are then contacted with tissue or cell samples suspected of abnormal raf expression and the sample is washed to remove unbound oligonucleotide. Radioactivity remaining in the sample indicates bound oligonucleotide (which in turn indicates the presence of raf) and can be quantitated using a scintillation counter or other routine means. Abnormally high levels of raf expression can be detected in this way. Double-labeling can be used with oligonucleotides and methods of the invention to specifically detect expression of truncated raf. Radiolabeled oligo can also be used to perform autoradiography of tissues to determine the localization, distribution and quantitation of abnormal raf expression for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing raf. Quantitation of the silver grains permits abnormally high levels of raf expression to be detected.

Analogous assays for fluorescent detection of raf expression can be developed using oligonucleotides of the invention which are conjugated with fluorescein or other fluorescent tag instead of radiolabeling. Such conjugations are routinely accomplished during solid phase synthesis using fluorescently labeled amidites or CPG (e.g., fluorescein-labeled amidites and CPG available from Glen Research, Sterling Va. See 1993 Catalog of Products for DNA Research, Glen Research, Sterling Va., p. 21). Double labeling can be used with oligonucleotides and methods of the invention to specifically detect expression of truncated raf.

Each of these assay formats is known in the art. One of skill could easily adapt these known assays for detection of abnormal raf expression in accordance with the teachings of the invention providing a novel and useful means to detect raf expression.

Oligonucleotide inhibition of c-raf expression:

The oligonucleotides shown in Table 1 were designed using the Genbank c-raf sequence HUMRAFR (Genbank listing x03484), synthesized and tested for inhibition of c-raf mRNA expression in T24 bladder carcinoma cells using a Northern blot assay. All are oligodeoxynucleotides with phosphorothioate backbones.

TABLE 1

Human c-raf Kinase Antisense Oligonucleotides

| Isis # | Sequence (5' → 3') | Site | SEQ ID NO: |
|---|---|---|---|
| 5000 | TGAAGGTGAGCTGGAGCCAT | Coding | 1 |
| 5074 | GCTCCATTGATGCAGCTTAA | AUG | 2 |
| 5075 | CCCTGTATGTGCTCCATTGA | AUG | 3 |
| 5076 | GGTGCAAAGTCAACTAGAAG | STOP | 4 |
| 5097 | ATTCTTAAACCTGAGGGAGC | 5'UTR | 5 |
| 5098 | GATGCAGCTTAAACAATTCT | 5'UTR | 6 |
| 5131 | CAGCACTGCAAATGGCTTCC | 3'UTR | 7 |
| 5132 | TCCCGCCTGTGACATGCATT | 3'UTR | 8 |
| 5133 | GCCGAGTGCCTTGCCTGGAA | 3'UTR | 9 |
| 5148 | AGAGATGCAGCTGGAGCCAT | Coding | 10 |
| 5149 | AGGTGAAGGCCTGGAGCCAT | Coding | 11 |
| 6721 | GTCTGGCGCTGCACCACTCT | 3'UTR | 12 |
| 6722 | CTGATTTCCAAAATCCCATG | 3'UTR | 13 |
| 6731 | CTGGGCTGTTTGGTGCCTTA | 3'UTR | 14 |
| 6723 | TCAGGGCTGGACTGCCTGCT | 3'UTR | 15 |
| 7825 | GGTGAGGGAGCGGGAGGCGG | 5'UTR | 16 |
| 7826 | CGCTCCTCCTCCCCGCGGCG | 5'UTR | 17 |
| 7827 | TTCGGCGGCAGCTTCTCGCC | 5'UTR | 18 |
| 7828 | GCCGCCCCAACGTCCTGTCG | 5'UTR | 19 |
| 7848 | TCCTCCTCCCCGCGGCGGGT | 5'UTR | 20 |
| 7849 | CTCGCCCGCTCCTCCTCCCC | 5'UTR | 21 |
| 7847 | CTGGCTTCTCCTCCTCCCCT | 3'UTR | 22 |
| 8034 | CGGGAGGCGGTCACATTCGG | 5'UTR | 23 |
| 8094 | TCTGGCGCTGCACCACTCTC | 3'UTR | 24 |

In a first round screen of oligonucleotides at concentrations of 100 nM or 200 nM, oligonucleotides 5074, 5075, 5132, 8034, 7826, 7827 and 7828 showed at least 50% inhibition of c-raf mRNA and these oligonucleotides are therefore preferred. Oligonucleotides 5132 and 7826 (SEQ ID NO: 8 and SEQ ID NO: 17) showed greater than about 90% inhibition and are more preferred. In additional assays, oligonucleotides 6721, 7848, 7847 and 8094 decreased c-raf mRNA levels by greater than 50%. These oligonucleotides are also preferred. Of these, 7847 (SEQ ID NO: 22) showed greater than about 90% inhibition of c-raf mRNA and is more preferred.

Specificity of ISIS 5132 for raf:

Specificity of ISIS 5132 for raf mRNA was demonstrated by a Northern blot assay in which this oligonucleotide was tested for the ability to inhibit Ha-ras mRNA as well as c-raf mRNA in T24 cells. Ha-ras is another naturally occurring cellular oncogene. ISIS 5132 was shown to abolish c-raf mRNA almost completely with no effect on Ha-ras mRNA levels.

2'-modified oligonucleotides:

Certain of these oligonucleotides were synthesized with either phosphodiester (P=O) or phosphorothioate (P=S) backbones and were also uniformly substituted at the 2' position of the sugar with either a 2'-O-methyl, 2'-O-propyl, or 2'-fluoro group. Oligonucleotides are shown in Table 2.

TABLE 2

Uniformly 2' Sugar-modified c-raf Oligonucleotides

| ISIS # | Sequence | Site | Modif. | SEQ ID NO: |
|---|---|---|---|---|
| 6712 | TCCCGCCTGTGACATGCATT | 3'UTR | OMe/P=S | 8 |
| 8033 | CGGGAGGCGGTCACATTCGG | 5'UTR | OMe/P=S | 23 |
| 7829 | GGTGAGGGAGCGGGAGGCGG | 5'UTR | OMe/P=S | 16 |
| 7830 | CGCTCCTCCTCCCCGCGGCG | 5'UTR | OMe/P=S | 17 |
| 7831 | TTCGGCGGCAGCTTCTCGCC | 5'UTR | OMe/P=S | 18 |
| 7832 | GCCGCCCCAACGTCCTGTCG | 5'UTR | OMe/P=S | 19 |
| 7833 | ATTCTTAAACCTGAGGGAGC | 5'UTR | OMe/P=S | 5 |
| 7834 | GATGCAGCTTAAACAATTCT | 5'UTR | OMe/P=S | 6 |
| 7835 | GCTCCATTGATGCAGCTTAA | AUG | OMe/P=S | 2 |
| 7836 | CCCTGTATGTGCTCCATTGA | AUG | OMe/P=S | 3 |
| 8035 | CGGGAGGCGGTCACATTCGG | 5'UTR | OPr/P=O | 23 |
| 7837 | GGTGAGGGAGCGGGAGGCGG | 5'UTR | OPr/P=O | 16 |
| 7838 | CGCTCCTCCTCCCCGCGGCG | 5'UTR | OPr/P=O | 17 |
| 7839 | TTCGGCGGCAGCTTCTCGCC | 5'UTR | OPr/P=O | 18 |
| 7840 | GCCGCCCCAACGTCCTGTCG | 5'UTR | OPr/P=O | 19 |
| 7841 | ATTCTTAAACCTGAGGGAGC | 5'UTR | OPr/P=O | 5 |
| 7842 | GATGCAGCTTAAACAATTCT | 5'UTR | OPr/P=O | 6 |
| 7843 | GCTCCATTGATGCAGCTTAA | AUG | OPr/P=O | 2 |
| 7844 | CCCTGTATGTGCTCCATTGA | AUG | OPr/P=O | 3 |
| 9355 | CGGGAGGCGGTCACATTCGG | 5'UTR | 2'F/P=S | 23 |

Oligonucleotides from Table 2 having uniform 2'O-methyl modifications and a phosphorothioate backbone were tested for ability to inhibit c-raf protein expression in T24 cells as determined by Western blot assay. Oligonucleotides 8033, 7834 and 7835 showed the greatest inhibition and are preferred. Of these, 8033 and 7834 are more preferred.

Chimeric oligonucleotides:

Chimeric oligonucleotides having SEQ ID NO: 8 were prepared. These oligonucleotides had central "gap" regions of 6, 8, or 10 deoxynucleotides flanked by two regions of 2'-O-methyl modified nucleotides. Backbones were uniformly phosphorothioate. In Northern blot analysis, all three of these oligonucleotides (ISIS 6720, 6-deoxy gap; ISIS 6717, 8-deoxy gap; ISIS 6729, 10-deoxy gap) showed greater than 70% inhibition of c-raf mRNA expression in T24 cells. These oligonucleotides are preferred. The 8-deoxy gap compound (6717) showed greater than 90% inhibition and is more preferred.

Additional chimeric oligonucleotides were synthesized having one or more regions of 2'-O-methyl modification and uniform phosphorothioate backbones. These are shown in Table 3. All are phosphorothioates; bold regions indicate 2'-O-methyl modified regions.

TABLE 3

Chimeric 2'-O-methyl P=S c-raf oligonucleotides

| Isis # | Sequence | Target site | SEQ ID NO: |
|---|---|---|---|
| 7848 | TCCTCCTCCCCGCGGCGGGT | 5'UTR | 20 |
| 7852 | TCCTCCTCCCCGCGGCGGGT | 5'UTR | 20 |
| 7849 | CTCGCCCGCTCCTCCTCCCC | 5'UTR | 21 |
| 7851 | CTCGCCCGCTCCTCCTCCCC | 5'UTR | 21 |
| 7856 | TTCTCGCCCGCTCCTCCTCC | 5'UTR | 25 |
| 7855 | TTCTCGCCCGCTCCTCCTCC | 5'UTR | 25 |
| 7854 | TTCTCCTCCTCCCCTGGCAG | 3'UTR | 26 |
| 7847 | CTGGCTTCTCCTCCTCCCCT | 3'UTR | 22 |
| 7850 | CTGGCTTCTCCTCCTCCCCT | 3'UTR | 22 |
| 7853 | CCTGCTGGCTTCTCCTCCTC | 3'UTR | 27 |

When tested for their ability to inhibit c-raf mRNA by Northern blot analysis, ISIS 7848, 7849, 7851, 7856, 7855, 7854, 7847, and 7853 gave better than 70% inhibition and are therefore preferred. Of these, 7851, 7855, 7847 and 7853 gave greater than 90% inhibition and are more preferred.

Additional chimeric oligonucleotides with various 2' modifications were prepared and tested. These are shown in Table 4. All are phosphorothioates; bold regions indicate 2'-modified regions.

TABLE 4

Chimeric 2'-modified P=S c-raf oligonucleotides

| Isis # | Sequence | Target site | Modif. | SEQ ID |
|---|---|---|---|---|
| 6720 | TCCCGCCTGTGACATGCATT | 3'UTR | 2'-O—Me | 8 |
| 6717 | TCCCGCCTGTGACATGCATT | 3'UTR | 2'-O—Me | 8 |
| 6729 | TCCCGCCTGTGACATGCATT | 3'UTR | 2'-O—Me | 8 |
| 8097 | TCTGGCGCTGCACCACTCTC | 3'UTR | 2'-O—Me | 24 |
| 9270 | TCCCGCCTGTGACATGCATT | 3'UTR | 2'-O—Pro | 8 |
| 9058 | TCCCGCCTGTGACATGCATT | 3'UTR | 2'-F | 8 |
| 9057 | TCTGGCGCTGCACCACTCTC | 3'UTR | 2'-F | 24 |

Of these, oligonucleotides 6720, 6717, 6729, 9720 and 9058 are preferred. Oligonucleotides 6717, 6729, 9720 and 9058 are more preferred.

Two chimeric oligonucleotides with 2'-O-propyl sugar modifications and chimeric P=O/P=S backbones were also synthesized. These are shown in Table 5, in which italic regions indicate regions which are both 2'-modified and have phosphodiester backbones.

TABLE 5

| Chimeric 2'-modified P=S/P=O c-raf oligonucleotides | | | | |
|---|---|---|---|---|
| Isis # | Sequence | Target site | Modif. | SEQ ID |
| 9271 | TCCCGCCTGTGACATGCATT | 3'UTR | 2'-O—Pro | 8 |
| 8096 | TCTGGCGCTGCACCACTCTC | 3'UTR | 2'-O—Pro | 24 |

Inhibition of cancer cell proliferation:

The phosphorothioate oligonucleotide ISIS 5132 was shown to inhibit T24 bladder cancer cell proliferation. Cells were treated with various concentrations of oligonucleotide in conjunction with LIPOFECTIN (a 1:1 liposome formulation of the cationic lipid N-[1-( 2,3-dioleyloxy) propyl]-N,N,N-trimethylammonium chloride (DOTMA) and dioleoyl phosphatidylethanolamine (DOPE)) (cationic lipid which increases uptake of oligonucleotide). A dose-dependent inhibition of cell proliferation was demonstrated, as indicated in Table 6, in which "None" indicates untreated control (no oligonucleotide) and "Control" indicates treatment with negative control oligonucleotide. Results are shown as percent inhibition compared to untreated control.

TABLE 6

| Inhibition of T24 Cell Proliferation by ISIS 5132 | | | |
|---|---|---|---|
| Oligo conc. | None | Control | 5132 |
| 50 nM | 0 | +9% | 23% |
| 100 nM | 0 | +4% | 24% |
| 250 nM | 0 | 10% | 74% |
| 500 nM | 0 | 18% | 82% |

Effect of ISIS 5132 on T24 human bladder carcinoma tumors:

Subcutaneous human T24 bladder carcinoma xenografts in nude mice were established and treated with ISIS 5132 and an unrelated control phosphorothioate oligonucleotide administered intraperitoneally three times weekly at a dosage of 25 mg/kg. In this preliminary study, ISIS 5132 inhibited tumor growth after eleven days by 35% compared to controls. Oligonucleotide-treated tumors remained smaller than control tumors throughout the course of the study.

Effect of ISIS 5132 on MDA-MB 231 human breast carcinoma tumors:

Subcutaneous human MDA-MB 231 breast carcinoma xenografts in nude mice were established and treated with ISIS 5132 and an unrelated control phosphorothioate oligonucleotide administered intravenously once per day at a dosage of 0.6 mg/kg or 6.0 mg/kg. ISIS 5132 inhibited tumor growth after 27 days (end of study) by approximately 80% compared to controls.

ISIS 5132 was also effective when administered intraperitoneally to MDA-MB 231 xenografts in nude mice. Oligonucleotide was administered once per day at 0.6 mg/kg or 6.0 mg/kg. By day 27 (end of study), tumor volume was inhibited by 57% (0.6 mg/kg dose) or 64% (6.0 mg/kg) compared to control.

Effect of ISIS 5132 on Colo 205 human colon carcinoma tumors:

Subcutaneous human Colo 205 colon carcinoma xenografts in nude mice were established and treated with ISIS 5132 and an unrelated control phosphorothioate oligonucleotide administered intravenously once per day at a dosage of 6.0 mg/kg. In this study, ISIS 5132 inhibited tumor growth after 25 days by over 40% compared to controls.

Antisense oligonucleotides targeted to A-raf:

It is believed that certain oligonucleotides targeted to portions of the A-raf mRNA and which inhibit A-raf expression will be useful for interfering with cell hyperproliferation. Methods for inhibiting A-raf expression using such antisense oligonucleotides are, likewise, believed to be useful for interfering with cell hyperproliferation.

The phosphorothioate deoxyoligonucleotides shown in Table 7 were designed and synthesized using the Genbank A-raf sequence HUMARAFIR (Genbank listing x04790).

TABLE 7

| Oligonucleotides Targeted to Human A-raf | | | | | | | | | |
|---|---|---|---|---|---|---|---|---|---|
| Isis # | Sequence | | | | | | | Site | SEQ ID NO: |
| 9060 | GTC | AAG | ATG | GGC | TGA | GGT | GG | 5' UTR | 28 |
| 9061 | CCA | TCC | CGG | ACA | GTC | ACC | AC | Coding | 29 |
| 9062 | ATG | AGC | TCC | TCG | CCA | TCC | AG | Coding | 30 |
| 9063 | AAT | GCT | GGT | GGA | ACT | TGT | AG | Coding | 31 |
| 9064 | CCG | GTA | CCC | CAG | GTT | CTT | CA | Coding | 32 |
| 9065 | CTG | GGC | AGT | CTG | CCG | GGC | CA | Coding | 33 |
| 9066 | CAC | CTC | AGC | TGC | CAT | CCA | CA | Coding | 34 |
| 9067 | GAG | ATT | TTG | CTG | AGG | TCC | GG | Coding | 35 |
| 9068 | GCA | CTC | CGC | TCA | ATC | TTG | GG | Coding | 36 |
| 9069 | CTA | AGG | CAC | AAG | GCG | GGC | TG | Stop | 37 |
| 9070 | ACG | AAC | ATT | GAT | TGG | CTG | GT | 3' UTR | 38 |
| 9071 | GTA | TCC | CCA | AAG | CCA | AGA | GG | 3' UTR | 39 |

The invention is further illustrated by the following examples which are illustrations only and are not intended to limit the present invention to specific embodiments.

EXAMPLES

Example 1

Synthesis and Characterization of Oligonucleotides

Unmodified DNA oligonucleotides were synthesized on an automated DNA synthesizer (Applied Biosystems model 380B) using standard phosphoramidite chemistry with oxidation by iodine. β-cyanoethyldiisopropyl phosphoramidites were purchased from Applied Biosystems (Foster City, Calif.). For phosphorothioate oligonucleotides, the standard oxidation bottle was replaced by a 0.2M solution of H-1,2-benzodithiole- 3-one 1,1-dioxide in acetonitrile for the stepwise thiation of the phosphite linkages. The thiation cycle wait step was increased to 68 seconds and was followed by the capping step. 2'-O-methyl phosphorothioate oligonucleotides were synthesized using 2'-O-methyl β-cyanoethyldiisopropyl-phosphoramidites (Chemgenes, Needham Mass.) and the standard cycle for unmodified oligonucleotides, except the wait step after pulse delivery of tetrazole and base was increased to 360 seconds. The 3'-base used to start the synthesis was a 2'-deoxyribonucleotide. 2'-O-propyl oligonucleotides were prepared by a slight modification of this procedure.

2'-fluoro phosphorothioate oligonucleotides were synthesized using 5'-dimethoxytrityl-3'-phosphoramidites and prepared as disclosed in U.S. patent application Ser. No. 463,358, filed Jan. 11, 1990, and Ser. No. 566,977, filed Aug. 13, 1990, which are assigned to the same assignee as the instant application and which are incorporated by reference herein. The 2'-fluoro oligonucleotides were prepared using phosphoramidite chemistry and a slight modification of the standard DNA synthesis protocol: deprotection was effected using methanolic ammonia at room temperature.

After cleavage from the controlled pore glass column (Applied Biosystems) and deblocking in concentrated ammonium hydroxide at 55° C for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0. Oligodeoxynucleotides and their phosphorothioate analogs were judged from electrophoresis to be greater than 80% full length material.

Example 2

Northern Blot Analysis of Inhibition of c-raf mRNA Expression

The human urinary bladder cancer cell line T24 was obtained from the American Type Culture Collection (Rockville Md.). Cells were grown in McCoy's 5A medium with L-glutamine (Gibco BRL, Gaithersburg Md.), supplemented with 10% heat-inactivated fetal calf serum and 50 U/ml each of penicillin and streptomycin. Cells were seeded on 100 mm plates. When they reached 70% confluency, they were treated with oligonucleotide. Plates were washed with 10 ml prewarmed PBS and 5 ml of Opti-MEM reduced-serum medium containing 2.5 µl DOTMA. Oligonucleotide with LIPOFECTIN (a 1:1 liposome formulation of the cationic lipid N-[1-( 2,3-dioleyloxy)propyl]-N,N,N-trimethylammonium chloride (DOTMA) and dioleoyl phosphatidylethanolamine (DOPE)) was then added to the desired concentration. After 4 hours of treatment, the medium was replaced with McCoy's medium. Cells were harvested 24 to 72 hours after oligonucleotide treatment and RNA was isolated using a standard CsCl purification method. Kingston, R. E., in *Current Protocols in Molecular Biology*, (F. M. Ausubel, R. Brent, R. E. Kingston, D. D. Moore, J. A. Smith, J. G. Seidman and K. Strahl, eds.), John Wiley and Sons, N.Y. Total RNA was isolated by centrifugation of cell lysates over a CsCl cushion. RNA samples were electrophoresed through 1.2% agarose-formaldehyde gels and transferred to hybridization membranes by capillary diffusion over a 12–14 hour period. The RNA was cross-linked to the membrane by exposure to UV light in a Stratalinker (Stratagene, La Jolla, Calif.) and hybridized to random-primed $^{32}$P-labeled c-raf cDNA probe (obtained from ATCC) or G3PDH probe as a control. RNA was quantitated using a Phosphorimager (Molecular Dynamics, Sunnyvale, Calif.).

Example 3

Specific Inhibition of c-raf Kinase Protein Expression in T24 Cells

T24 cells were treated with oligonucleotide (200 nM) and LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE)) at T=0 and T=24 hours. Protein extracts were prepared at T=48 hours, electrophoresed on acrylamide gels and analyzed by Western blot using polyclonal antibodies against c-raf (UBI, Lake Placid, N.Y.) or A-raf (Transduction Laboratories, Knoxville, Tenn.). Radiolabeled secondary antibodies were used and raf protein was quantitated using a Phosphorimager (Molecular Dynamics, Sunnyvale Calif.).

Example 4

Antisense Inhibition of Cell Proliferation

T24 cells were treated on day 0 for two hours with various concentrations of oligonucleotide and LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE)) (50 nM oligonucleotide in the presence of 2 µg/ml LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE)) 100 nM oligonucleotide and 2µg/ml LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE)); 250 nM oligonucleotide and 6 µg/ml LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE)) or 500 nM oligonucleotide and 10 µg/ml LIPOFECTIN (a 1:1 liposome formulation of the cationic lipid N-[1-(2,3-dioleyloxy)propyl]-N,N,N-trimethylammonium chloride (DOTMA) and dioleoyl phosphatidylethanolamine (DOPE))). On day 1, cells were treated for a second time at desired oligonucleotide concentration for two hours. On day 2, cells were counted.

Example 5

Effect of ISIS 5132 on T24 Human Bladder Carcinoma Tumor Xenografts in Nude Mice

$5 \times 10^6$ T24 cells were implanted subcutaneously in the right inner thigh of nude mice. Oligonucleotides (ISIS 5132 and an unrelated control phosphorothioate oligonucleotide suspended in saline) were administered three times weekly beginning on day 4 after tumor cell inoculation. A saline-only control was also given. Oligonucleotides were given by intraperitoneal injection. Oligonucleotide dosage was 25 mg/kg. Tumor size was measured and tumor volume was calculated on the eleventh, fifteenth and eighteenth treatment days.

Example 6

Effect of ISIS 5132 on MDA-MB 231 Human Breast Carcinoma Tumor Xenografts in Nude Mice

$5 \times 10^6$ MDA-MB 231 cells were implanted subcutaneously in the right inner thigh of nude mice. Oligonucleotides (ISIS 5132 and an unrelated control phosphorothioate oligonucleotide suspended in saline) were administered once daily beginning on day 10 after tumor cell inoculation. A saline-only control was also given. Oligonucleotides were given by intravenous injection at a dosage of 0.6 mg/kg or 6.0 mg/kg. Tumor size was measured and tumor volume was calculated on days 10, 13, 16, 20, 23 and 27 following tumor cell inoculation.

For intraperitoneal oligonucleotide administration, oligonucleotides were administered once daily beginning on day 10 after tumor cell inoculation. A saline-only control was also given. Oligonucleotides were given by intraperitoneal injection at a dosage of 0.6 mg/kg or 6.0 mg/kg. Tumor size was measured and tumor volume was calculated on days 10, 13, 16, 20, 23 and 27 following tumor cell inoculation.

Example 7

Effect of ISIS 5132 on Colo 205 Human Colon Carcinoma Tumor Xenografts in Nude Mice

$5 \times 10^6$ Colo 205 cells were implanted subcutaneously in the right inner thigh of nude mice. Oligonucleotides (ISIS 5132 and an unrelated control phosphorothioate oligonucleotide suspended in saline) were administered once per day beginning on day 5 after tumor cell inoculation. A saline-only control was also given. Oligonucleotides were given by intravenous injection. Oligonucleotide dosage was 6 mg/kg. Tumor size was measured and tumor volume was calculated on days 5, 8, 11, 14, 18, 22 and 25 after tumor inoculation.

Example 8

Diagnostic Assay for raf-associated Tumors Using Xenografts in Nude Mice

Tumors arising from abnormal raf expression are diagnosed and distinguished from other tumors using this assay. A biopsy sample of the tumor is treated, e.g., with collagenase or trypsin or other standard methods, to dissociate the tumor mass. $5 \times 10^6$ tumor cells are implanted subcutaneously in the inner thighs of two or more nude mice. Antisense oligonucleotide (e.g., ISIS 5132) suspended in saline is administered to one or more mice by intraperitoneal injection three times weekly beginning on day 4 after tumor cell inoculation. Saline only is given to a control mouse. Oligonucleotide dosage is 25 mg/kg. Tumor size is measured and tumor volume is calculated on the eleventh treatment day. Tumor volume of the oligonucleotide-treated mice is compared to that of the control mouse. The volume of raf-associated tumors in the treated mice are measurably smaller than tumors in the control mouse. Tumors arising from causes other than abnormal raf expression are not expected to respond to the oligonucleotides targeted to raf and, therefore, the tumor volumes of oligonucleotide-treated and control mice are equivalent.

Example 9

Detection of Abnormal raf Expression

Oligonucleotides are radiolabeled after synthesis by $^{32}P$ labeling at the 5' end with polynucleotide kinase. Sambrook et al., *Molecular Cloning. A Laboratory Manual*, Cold Spring Harbor Laboratory Press, 1989, Volume 2, pg. 11.31–11.32. Radiolabeled oligonucleotides are contacted with tissue or cell samples suspected of abnormal raf expression, such as tumor biopsy samples or skin samples where psoriasis is suspected, under conditions in which specific hybridization can occur, and the sample is washed to remove unbound oligonucleotide. Radioactivity remaining in the sample indicates bound oligonucleotide and is quantitated using a scintillation counter or other routine means.

Radiolabeled oligonucleotides of the invention are also used in autoradiography. Tissue sections are treated with radiolabeled oligonucleotide and washed as described above, then exposed to photographic emulsion according to standard autoradiography procedures. The emulsion, when developed, yields an image of silver grains over the regions expressing raf. The extent of raf expression is determined by quantitation of the silver grains.

Analogous assays for fluorescent detection of raf expression use oligonucleotides of the invention which are labeled with fluorescein or other fluorescent tags. Labeled DNA oligonucleotides are synthesized on an automated DNA synthesizer (Applied Biosystems model 380B) using standard phosphoramidite chemistry with oxidation by iodine. β-cyanoethyldiisopropyl phosphoramidites are purchased from Applied Biosystems (Foster City, Calif.). Fluorescein-labeled amidites are purchased from Glen Research (Sterling Va.). Incubation of oligonucleotide and biological sample is carried out as described for radiolabeled oligonucleotides except that instead of a scintillation counter, a fluorimeter or fluorescence microscope is used to detect the fluorescence which indicates raf expression.

Example 10

Detection of Truncated Activated raf Expression

Tissue or cell samples suspected of expressing truncated raf, such as tumor biopsy samples or skin samples where psoriasis is suspected, are incubated with a $^{32}P$ or fluorescein-labeled oligonucleotide which is targeted to the 3' untranslated region of raf mRNA. An identical sample of cells or tissues is incubated with a second labeled oligonucleotide which is targeted to the 5' untranslated region or translation initiation site of raf mRNA, under conditions in which specific hybridization can occur, and the sample is washed to remove unbound oligonucleotide. Label remaining in the sample indicates bound oligonucleotide and can be quantitated using a scintillation counter, fluorimeter, or other routine means. The presence of activated truncated raf is indicated if the first sample does not bind labeled oligonucleotide and the second oligonucleotide does retain label.

Double labeling can also be used with oligonucleotides and methods of the invention to specifically detect expression of activated truncated raf. A single tissue sample is incubated with a $^{32}$P-labeled oligonucleotide which is targeted to the 3' untranslated region of raf mRNA and a fluorescein-labeled oligonucleotide which is targeted to the 5' untranslated region or translation initiation site of raf mRNA, under conditions in which specific hybridization can occur. The sample is washed to remove unbound oligonucleotide and labels are detected by scintillation and fluorimetry. The presence of activated truncated raf is indicated if the sample does not bind $^{32}$P-labeled oligonucleotide (i.e., is not radioactive) but does retain the fluorescent label.

What is claimed is:

1. An oligonucleotide consisting of the sequence of SEQ. ID. NO: 2, 6, 8, 12, 17, 20, 21, 22, 23, 24, 25, 26, or 27.

2. The oligonucleotide of claim 1 comprising at least one phosphorothioate internucleoside linkage.

3. The oligonucleotide of claim 1 wherein at least one of the nucleotide units of the oligonucleotide is modified at the 2' position of the sugar moiety, said modification consisting of a 2'-O-fluoro, 2'-O-methyl, 2'-O-ethyl, or 2'-O-propyl moiety.

4. The oligonucleotide of claim 1 comprising at least one 2'-deoxynucleotide.

5. An oligonucleotide consisting of the sequence of SEQ. ID. NO: 8, 21, 24, 25, 26, or 27.

6. The oligonucleotide of claim 5 comprising at least one phosphorothioate internucleoside linkage.

7. The oligonucleotide of claim 5 wherein at least one of the nucleotide units of the oligonucleotide is modified at the 2' position of the sugar moiety, said modification consisting of a 2'-O-fluoro, 2'-O-methyl, 2'-O-ethyl, or 2'-O-propyl moiety.

8. The oligonucleotide of claim 5 comprising at least one 2'-deoxynucleotide.

9. An oligonucleotide consisting of the sequence of SEQ. ID. NO: 8.

10. The oligonucleotide of claim 9 comprising at least one phosphorothioate internucleoside linkage.

11. The oligonucleotide of claim 9 wherein at least one of the nucleotide units of the oligonucleotide is modified at the 2' position of the sugar moiety, said modification consisting of a 2'-O-fluoro, 2'-O-methyl, 2'-O-ethyl, or 2'-O-propyl moiety.

12. The oligonucleotide of claim 9 comprising at least one 2'-deoxynucleotide.

* * * * *

UNITED STATES PATENT AND TRADEMARK OFFICE
CERTIFICATE OF CORRECTION

PATENT NO. : 5,563,255
DATED : Oct. 8, 1996
INVENTOR(S) : Monia et al.

It is certified that error appears in the above-indentified patent and that said Letters Patent is hereby corrected as shown below:

Column 33, line 46, delete "2'-O-fluoro" and insert therefor --2'-fluoro--

Column 34, line 39, delete "2'-O-fluoro" and insert therefor --2'-fluoro--

Column 34, line 50, delete "2'-O-fluoro" and insert therefor --2'-fluoro--

Signed and Sealed this

Twenty-fifth Day of February, 1997

Attest:

BRUCE LEHMAN

*Attesting Officer*  *Commissioner of Patents and Trademarks*

SEQUENCE LISTING ( 1 ) GENERAL INFORMATION:

( i i i ) NUMBER OF SEQUENCES: 39

( 2 ) INFORMATION FOR SEQ ID NO: 1:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 1:

TGAAGGTGAG CTGGAGCCAT                              20

( 2 ) INFORMATION FOR SEQ ID NO: 2:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 2:

GCTCCATTGA TGCAGCTTAA                              20

( 2 ) INFORMATION FOR SEQ ID NO: 3:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 3:

CCCTGTATGT GCTCCATTGA                              20

( 2 ) INFORMATION FOR SEQ ID NO: 4:

( i ) SEQUENCE CHARACTERISTICS:
( A ) LENGTH: 20
( B ) TYPE: Nucleic Acid
( C ) STRANDEDNESS: Single
( D ) TOPOLOGY: Linear ( i v ) ANTI-SENSE: Yes ( x i ) SEQUENCE DESCRIPTION: SEQ ID NO: 4:

GGTGCAAAGT CAACTAGAAG                              20

( 2 ) INFORMATION FOR SEQ ID NO: 5:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 5:

ATTCTTAAAC CTGAGGGAGC          20

( 2 ) INFORMATION FOR SEQ ID NO: 6:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 6:

GATGCAGCTT AAACAATTCT          20

( 2 ) INFORMATION FOR SEQ ID NO: 7:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 7:

CAGCACTGCA AATGGCTTCC          20

( 2 ) INFORMATION FOR SEQ ID NO: 8:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 8:

TCCCGCCTGT GACATGCATT          20

( 2 ) INFORMATION FOR SEQ ID NO: 9:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 9:

GCCGAGTGCC TTGCCTGGAA          20

( 2 ) INFORMATION FOR SEQ ID NO: 10:

( i ) SEQUENCE CHARACTERISTICS:
    ( A ) LENGTH: 20
    ( B ) TYPE: Nucleic Acid
    ( C ) STRANDEDNESS: Single (D) TOPOLOGY: Linear (iv) ANTI-SENSE: Yes (xi) SEQUENCE DESCRIPTION: SEQ ID NO: 10:

AGAGATGCAG CTGGAGCCAT 20

(2) INFORMATION FOR SEQ ID NO: 11:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 11:

AGGTGAAGGC CTGGAGCCAT 20

(2) INFORMATION FOR SEQ ID NO: 12:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 12:

GTCTGGCGCT GCACCACTCT 20

(2) INFORMATION FOR SEQ ID NO: 13:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 13:

CTGATTTCCA AAATCCCATG 20

(2) INFORMATION FOR SEQ ID NO: 14:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 14:

CTGGGCTGTT TGGTGCCTTA 20

(2) INFORMATION FOR SEQ ID NO: 15:

(i) SEQUENCE CHARACTERISTICS:
(A) LENGTH: 20
(B) TYPE: Nucleic Acid
(C) STRANDEDNESS: Single
(D) TOPOLOGY: Linear (iv) ANTI-SENSE: Yes (xi) SEQUENCE DESCRIPTION: SEQ ID NO: 15:

TCAGGGCTGG ACTGCCTGCT                                                                                          20

( 2 ) INFORMATION FOR SEQ ID NO: 16:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 16:

GGTGAGGGAG CGGGAGGCGG                                                                                          20

( 2 ) INFORMATION FOR SEQ ID NO: 17:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 17:

CGCTCCTCCT CCCCGCGGCG                                                                                          20

( 2 ) INFORMATION FOR SEQ ID NO: 18:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 18:

TTCGGCGGCA GCTTCTCGCC                                                                                          20

( 2 ) INFORMATION FOR SEQ ID NO: 19:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 19:

GCCGCCCAA CGTCCTGTCG                                                                                           20

( 2 ) INFORMATION FOR SEQ ID NO: 20:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 20:

TCCTCCTCCC CGCGGCGGGT                                                                                          20

( 2 ) INFORMATION FOR SEQ ID NO: 21:

( i ) SEQUENCE CHARACTERISTICS:
    ( A ) LENGTH: 20
    ( B ) TYPE: Nucleic Acid
    ( C ) STRANDEDNESS: Single
    ( D ) TOPOLOGY: Linear ( i v ) ANTI-SENSE: Yes ( x i ) SEQUENCE DESCRIPTION: SEQ ID NO: 21:

CTCGCCCGCT CCTCCTCCCC     20

( 2 ) INFORMATION FOR SEQ ID NO: 22:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 22:

CTGGCTTCTC CTCCTCCCCT     20

( 2 ) INFORMATION FOR SEQ ID NO: 23:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 23:

CGGGAGGCGG TCACATTCGG     20

( 2 ) INFORMATION FOR SEQ ID NO: 24:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 24:

TCTGGCGCTG CACCACTCTC     20

( 2 ) INFORMATION FOR SEQ ID NO: 25:

( i ) SEQUENCE CHARACTERISTICS:
        ( A ) LENGTH: 20
        ( B ) TYPE: Nucleic Acid
        ( C ) STRANDEDNESS: Single
        ( D ) TOPOLOGY: Linear ( i v ) ANTI-SENSE: Yes ( x i ) SEQUENCE DESCRIPTION: SEQ ID NO: 25:

TTCTCGCCCG CTCCTCCTCC     20

( 2 ) INFORMATION FOR SEQ ID NO: 26:

( i ) SEQUENCE CHARACTERISTICS:
        ( A ) LENGTH: 20
        ( B ) TYPE: Nucleic Acid
        ( C ) STRANDEDNESS: Single (D) TOPOLOGY: Linear (iv) ANTI-SENSE: Yes (xi) SEQUENCE DESCRIPTION: SEQ ID NO: 26:

TTCTCCTCCT CCCCTGGCAG 20

(2) INFORMATION FOR SEQ ID NO: 27:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 27:

CCTGCTGGCT TCTCCTCCTC 20

(2) INFORMATION FOR SEQ ID NO: 28:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 28:

GTCAAGATGG GCTGAGGTGG 20

(2) INFORMATION FOR SEQ ID NO: 29:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 29:

CCATCCCGGA CAGTCACCAC 20

(2) INFORMATION FOR SEQ ID NO: 30:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 30:

ATGAGCTCCT CGCCATCCAG 20

(2) INFORMATION FOR SEQ ID NO: 31:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 31:

AATGCTGGTG GAACTTGTAG 20

(2) INFORMATION FOR SEQ ID NO: 32:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 32:

CCGGTACCCC AGGTTCTTCA 20

(2) INFORMATION FOR SEQ ID NO: 33:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 33:

CTGGGCAGTC TGCCGGGCCA 20

(2) INFORMATION FOR SEQ ID NO: 34:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 34:

CACCTCAGCT GCCATCCACA 20

(2) INFORMATION FOR SEQ ID NO: 35:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 35:

GAGATTTTGC TGAGGTCCGG 20

(2) INFORMATION FOR SEQ ID NO: 36:

(i) SEQUENCE CHARACTERISTICS:
        (A) LENGTH: 20
        (B) TYPE: Nucleic Acid
        (C) STRANDEDNESS: Single
        (D) TOPOLOGY: Linear (iv) ANTI-SENSE: Yes (xi) SEQUENCE DESCRIPTION: SEQ ID NO: 36:

GCACTCCGCT CAATCTTGGG 20

(2) INFORMATION FOR SEQ ID NO: 37:

( i ) SEQUENCE CHARACTERISTICS:
 ( A ) LENGTH: 20
 ( B ) TYPE: Nucleic Acid
 ( C ) STRANDEDNESS: Single
 ( D ) TOPOLOGY: Linear ( i v ) ANTI-SENSE: Yes ( x i ) SEQUENCE DESCRIPTION: SEQ ID NO: 37:

CTAAGGCACA AGGCGGGCTG 20

( 2 ) INFORMATION FOR SEQ ID NO: 38:

( i ) SEQUENCE CHARACTERISTICS:
 ( A ) LENGTH: 20
 ( B ) TYPE: Nucleic Acid
 ( C ) STRANDEDNESS: Single
 ( D ) TOPOLOGY: Linear ( i v ) ANTI-SENSE: Yes ( x i ) SEQUENCE DESCRIPTION: SEQ ID NO: 38:

ACGAACATTG ATTGGCTGGT 20

( 2 ) INFORMATION FOR SEQ ID NO: 39:

( i ) SEQUENCE CHARACTERISTICS:
 ( A ) LENGTH: 20
 ( B ) TYPE: Nucleic Acid
 ( C ) STRANDEDNESS: Single
 ( D ) TOPOLOGY: Linear ( i v ) ANTI-SENSE: Yes ( x i ) SEQUENCE DESCRIPTION: SEQ ID NO: 39:

GTATCCCCAA AGCCAAGAGG 20